US010024998B2

(12) United States Patent
Hills et al.

(10) Patent No.: US 10,024,998 B2
(45) Date of Patent: *Jul. 17, 2018

(54) GANTRY SYSTEM FOR CT IMAGING SYSTEM AND METHODS OF ASSEMBLING SAME

(71) Applicant: Morpho Detection, LLC, Newark, CA (US)

(72) Inventors: Steven Leslie Hills, San Jose, CA (US); Pedro Andres Garzon, Santa Clara, CA (US); Anthony James Murch, Hayward, CA (US)

(73) Assignee: SMITHS DETECTION, LLC, Newark, CA (US)

( * ) Notice: Subject to any disclaimer, the term of this patent is extended or adjusted under 35 U.S.C. 154(b) by 252 days.

This patent is subject to a terminal disclaimer.

(21) Appl. No.: 14/820,996

(22) Filed: Aug. 7, 2015

(65) Prior Publication Data

US 2017/0042008 A1    Feb. 9, 2017

(51) Int. Cl.
*H05G 1/02* (2006.01)
*G01V 5/00* (2006.01)
*A61B 6/03* (2006.01)

(52) U.S. Cl.
CPC ............... *G01V 5/005* (2013.01); *A61B 6/03* (2013.01)

(58) Field of Classification Search
CPC ........... G01N 23/046; G01N 2223/308; G01N 2223/419; A61B 6/035; H05G 1/02; G01V 5/005

See application file for complete search history.

(56) References Cited

U.S. PATENT DOCUMENTS

| | | | |
|---|---|---|---|
| 4,232,914 A | 11/1980 | Bowen, III | |
| 5,473,657 A | 12/1995 | McKenna | |
| 7,010,081 B2 | 3/2006 | Brunnett et al. | |
| 8,796,893 B2 | 8/2014 | Muth | |
| 9,568,441 B2 * | 2/2017 | Garzon | ................ G01N 23/046 |
| 2012/0148013 A1 | 6/2012 | Zhang et al. | |

OTHER PUBLICATIONS

U.S. Appl. No. 14/607,967, filed Jan. 28, 2015, entitled Gantry System for CT Imaging System and Methods of Assembling Same.

* cited by examiner

*Primary Examiner* — Courtney Thomas
(74) *Attorney, Agent, or Firm* — Armstrong Teasdale LLP (57) ABSTRACT

A gantry system for use with a computed tomography (CT) imaging system is provided. The gantry system includes a gantry assembly configured to rotate about a rotational axis to collect imaging data from an object. The gantry assembly includes a support rail. A radially inner surface of the support rail includes a canted first portion and an oppositely canted second portion. The gantry system also includes a plurality of roller assemblies rotatably supporting the gantry assembly. Each of the plurality of roller assemblies comprises a first roller sleeve configured to engage the first portion and a second roller sleeve configured to engage the second portion.

20 Claims, 9 Drawing Sheets

GANTRY SYSTEM FOR CT IMAGING SYSTEM AND METHODS OF ASSEMBLING SAME

BACKGROUND

The embodiments described herein relate generally to computed tomography (CT) imaging systems, and more particularly, to rotating gantry systems for use in CT imaging systems.

Some CT imaging systems include a gantry having an x-ray source and one or more x-ray detectors. The gantry has an opening defined therein, and rotates about a central rotational axis to capture imaging data on an object positioned within the gantry opening using the x-ray source and x-ray detectors. The gantry is typically mounted to the CT imaging system by a bearing system that enables the gantry to rotate.

The gantry is often rotated at significant speeds to facilitate the collection of accurate imaging data during a helical scan of an object. As a result, at least some known CT imaging systems utilize costly and complex bearing systems to enable gantry rotation. For example, some known CT imaging systems utilize slew- or roller-type bearing assemblies having numerous rolling elements disposed between two bearing rings. Such bearing assemblies often utilize a large number of rolling elements to enable high-speed rotation of the gantry. Additionally, the components of such bearing assemblies are often of significant size and, consequently, of significant cost. For example, bearing rings used in some gantry bearing assemblies have a diameter in excess of three feet. A tunnel size and a field of view of the CT imaging system may be limited by the size of the bearing assemblies, and repairing and replacing components on gantry bearing assemblies often requires significant time and cost.

Additionally, gantry bearing assemblies utilized in CT imaging systems often include custom-made components that are designed for a particular CT imaging system (e.g., CT imaging systems manufactured by a specific CT imaging system manufacturer). Such custom components are often not easily replaced or interchangeable with other, more readily available and less costly components, and thus further contribute to the cost and time associated with maintaining gantry systems in CT imaging systems.

BRIEF SUMMARY

In one aspect, a gantry system for use with a computed tomography (CT) imaging system is provided. The gantry system includes a gantry assembly configured to rotate about a rotational axis to collect imaging data from an object. The gantry assembly includes a support rail. A radially inner surface of the support rail includes a canted first portion and an oppositely canted second portion. The gantry system also includes a plurality of roller assemblies rotatably supporting the gantry assembly. Each of the plurality of roller assemblies comprises a first roller sleeve configured to engage the first portion and a second roller sleeve configured to engage the second portion.

In another aspect, a computed tomography (CT) imaging system is provided. The CT imaging system includes a base and a plurality of roller assemblies coupled to the base. Each of the plurality of roller assemblies includes a first roller sleeve and a second roller sleeve. The CT imaging system includes a gantry assembly rotatably coupled to the plurality of roller assemblies for rotation about a rotational axis. The gantry assembly includes a radiation source, at least one detector configured to detect radiation emitted by the radiation source, and a support rail that includes a radially inner surface. The radially inner surface includes a canted first portion engaged by the first roller sleeve of each roller assembly and an oppositely canted second portion engaged by the second roller sleeve of each roller assembly.

In yet another aspect, a method of assembling a CT imaging system is provided. The CT imaging system includes a base. The method includes coupling a plurality of roller assemblies to the base. Each of the plurality of roller assemblies includes a first roller sleeve and a second roller sleeve. The method also includes coupling a gantry assembly to the plurality of roller assemblies such that a canted first portion of a radially inner surface of a support rail of the gantry assembly is engaged by the first roller sleeve of each roller assembly, and an oppositely canted second portion of the radially inner surface is engaged by the second roller sleeve of each roller assembly.

DETAILED DESCRIPTION

Figure 1:
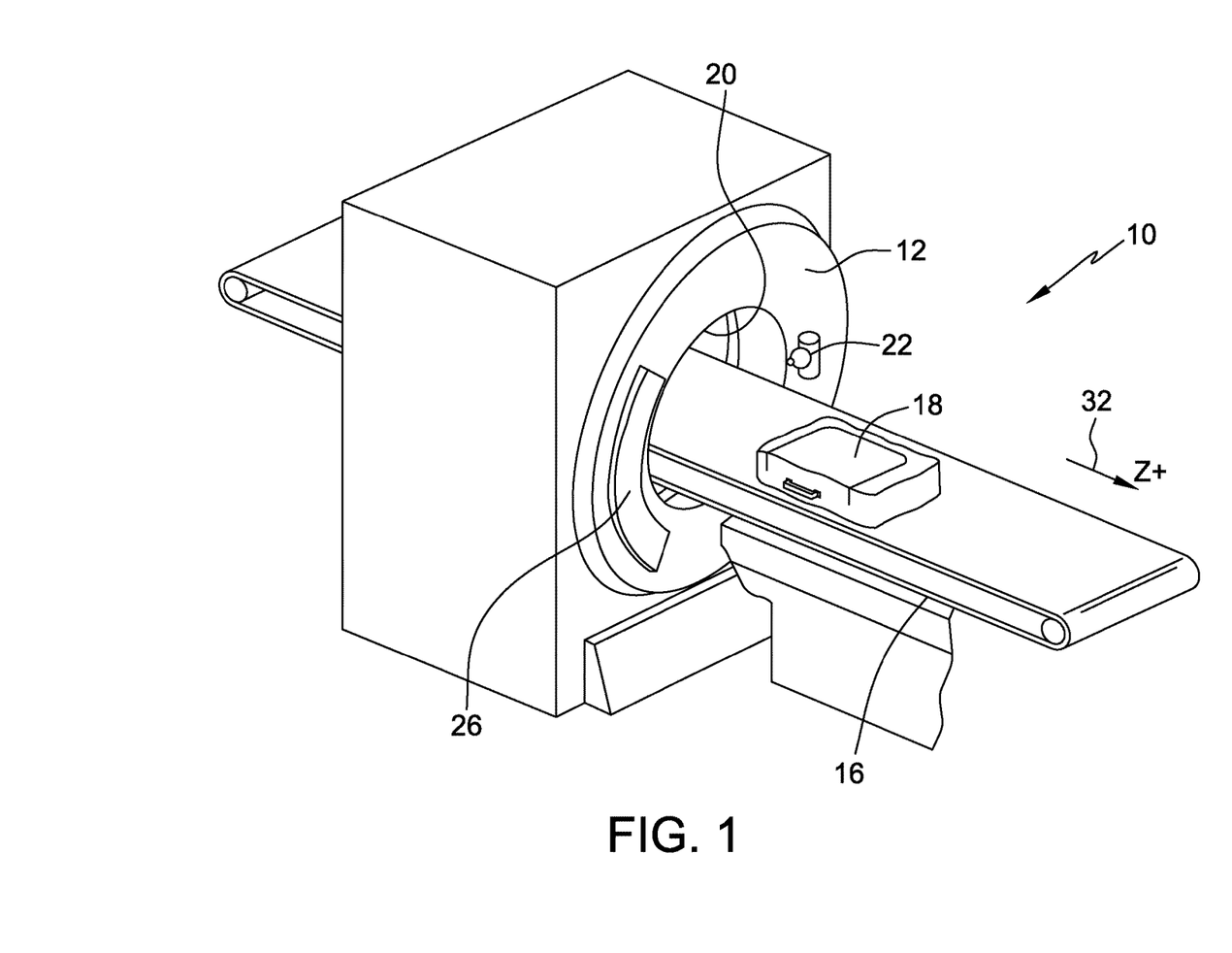
FIG. 1 is a perspective view of an exemplary CT imaging system.
Figure 2:
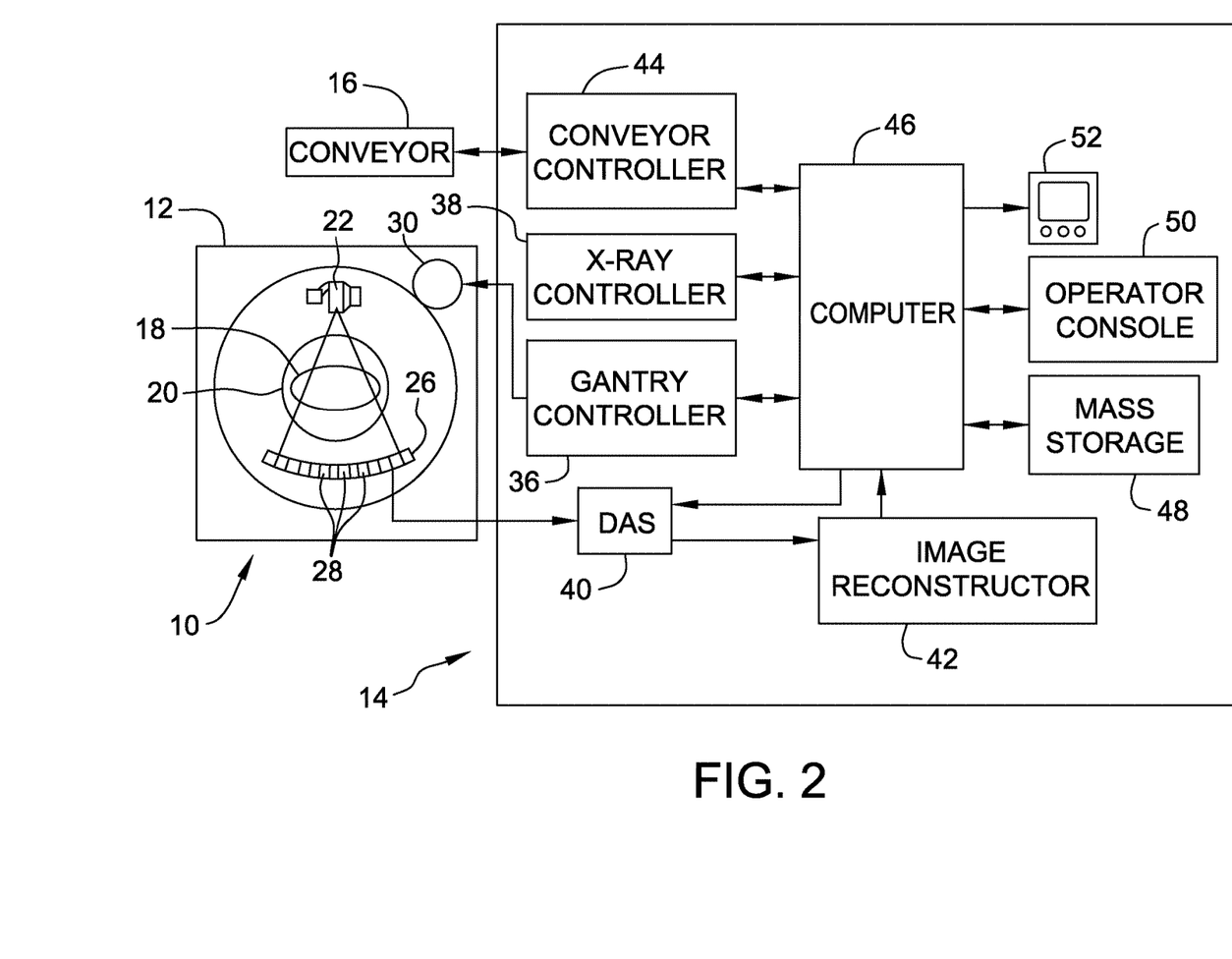
FIG. 2 is a schematic diagram of the CT imaging system shown in FIG. 1.

FIG. 1 is a perspective view of a computed tomography (CT) imaging system 10. FIG. 2 is a schematic diagram of CT imaging system 10 shown in FIG. 1. As shown in FIGS. 1 and 2, CT imaging system 10 includes a gantry system 12, which is representative of a CT scanner, a control system 14 (FIG. 2), and a motorized conveyor belt 16 for positioning an object 18, such as a piece of luggage, in a gantry opening 20 defined through gantry system 12. CT imaging system 10 may be, for example, a dual energy CT system. Gantry system 12 includes a radiation source 22 that projects a beam of radiation toward a detector array 26 on the opposite side of gantry system 12. In the exemplary embodiment, radiation source 22 is an x-ray source configured to emit a fan beam of x-rays. Detector array 26 is formed by detector elements 28 (FIG. 2). Detector elements 28 are radiation detectors that each produce a signal having a magnitude that represents and is dependent on the intensity of the attenuated x-ray beam after it has passed through object 18 being imaged. During a helical scan that acquires x-ray projection data, a drive mechanism 30 (FIG. 2) rotates gantry system 12 along with the radiation source 22 and detector array 26 within a plane and around object 18 about an axis of rotation, while object 18 is moved through gantry system 12 in a z-direction 32 perpendicular to the plane of rotation.

Gantry system 12 and radiation source 22 are controlled by control system 14, which includes a gantry controller 36, an x-ray controller 38, a data acquisition system (DAS) 40, an image reconstructor 42, a conveyor controller 44, a computer 46, a mass storage system 48, an operator console 50, and a display device 52. Gantry controller 36 is operably coupled to drive mechanism 30, and controls the rotational speed and position of gantry system 12, while x-ray controller 38 provides power and timing signals to radiation source 22, and data acquisition system 40 acquires analog data from detector elements 28 and converts the data to digital form for subsequent processing. Image reconstructor 42 receives the digitized x-ray data from data acquisition system 40 and performs an image reconstruction process that involves filtering the projection data using a helical reconstruction algorithm.

Computer 46 is in communication with the gantry controller 36, x-ray controller 38, and conveyor controller 44 whereby control signals are sent from computer 46 to controllers 36, 38, 44 and information is received from controllers 36, 38, 44 by computer 46. Computer 46 also provides commands and operational parameters to data acquisition system 40 and receives reconstructed image data from image reconstructor 42. The reconstructed image data is stored by computer 46 in mass storage system 48 for subsequent retrieval. An operator interfaces with computer 46 through operator console 50, which may include, for example, a keyboard and a graphical pointing device, and receives output, such as, for example, a reconstructed image, control settings and other information, on display device 52.

Communication between the various system elements of FIG. 2 is depicted by arrowhead lines, which illustrate a means for either signal communication or mechanical operation, depending on the system element involved. Communication amongst and between the various system elements may be obtained through a hardwired or a wireless arrangement. Computer 46 may be a standalone computer or a network computer and may include instructions in a variety of computer languages for use on a variety of computer platforms and under a variety of operating systems. Other examples of computer 46 include a system having a microprocessor, microcontroller or other equivalent processing device capable of executing commands of computer readable data or program for executing a control algorithm. In order to perform the prescribed functions and desired processing, as well as the computations therefore, computer 46 may include, for example and without limitation, a processor(s), memory, storage, register(s), timing, interrupt(s), communication interfaces, and input/output signal interfaces, as well as combinations including at least one of the foregoing. For example, computer 46 may include input signal filtering to enable accurate sampling and conversion or acquisitions of such signals from communications interfaces.

Figure 3:
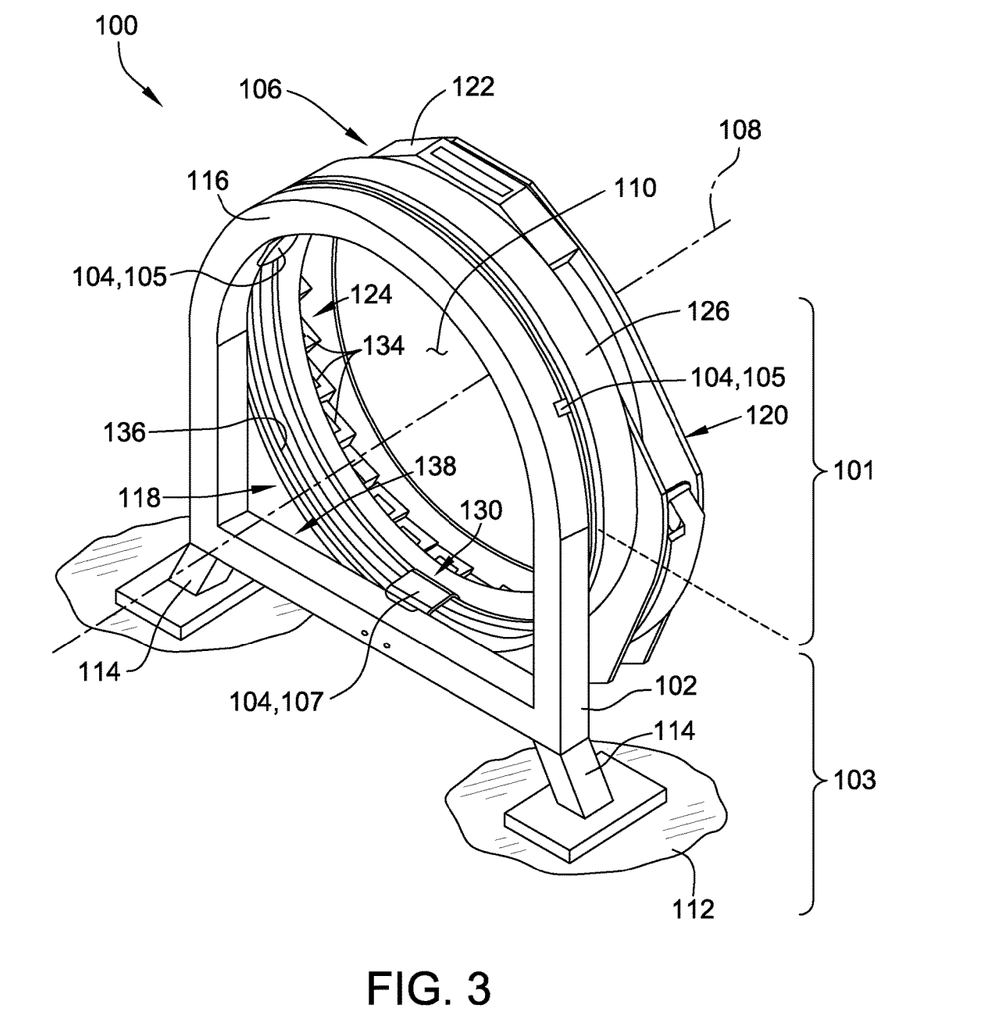
FIG. 3 is a front perspective view of an exemplary gantry system suitable for use in the CT imaging system of FIG. 1, the gantry system including a base and a gantry assembly.
Figure 4:
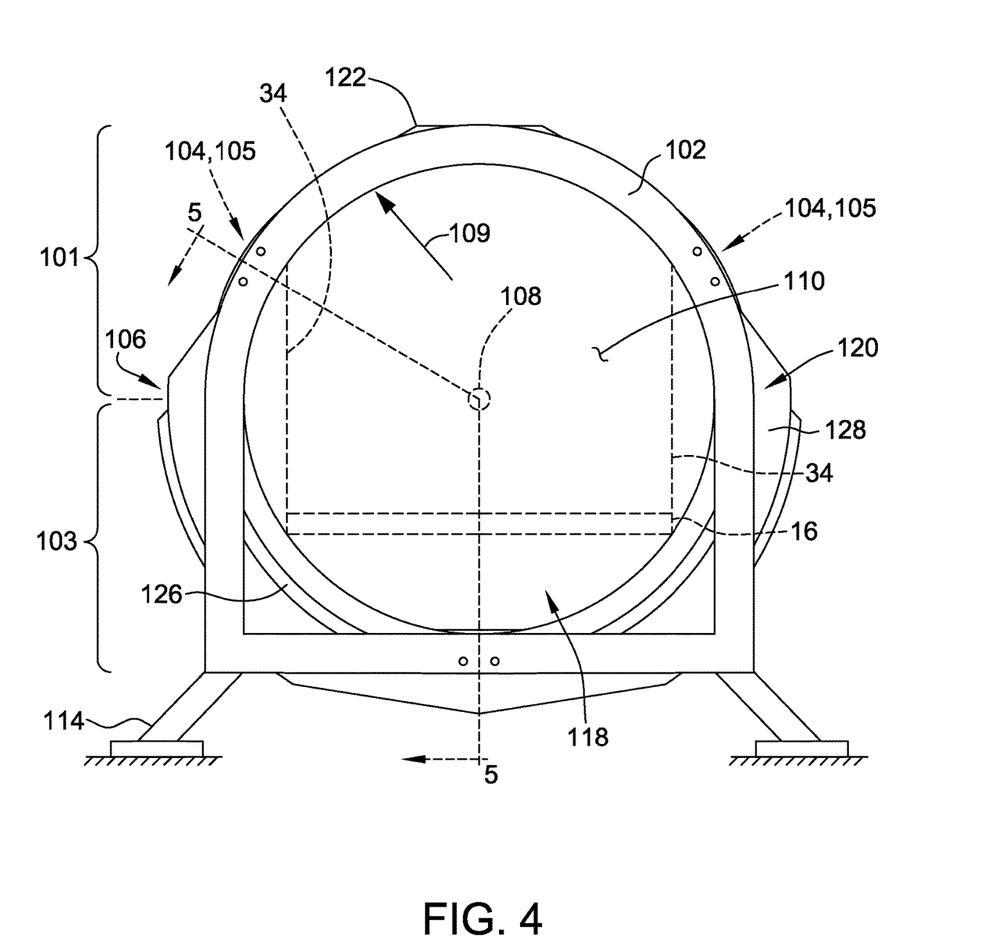
FIG. 4 is a rear view of the gantry system of FIG. 3.
Figure 5:
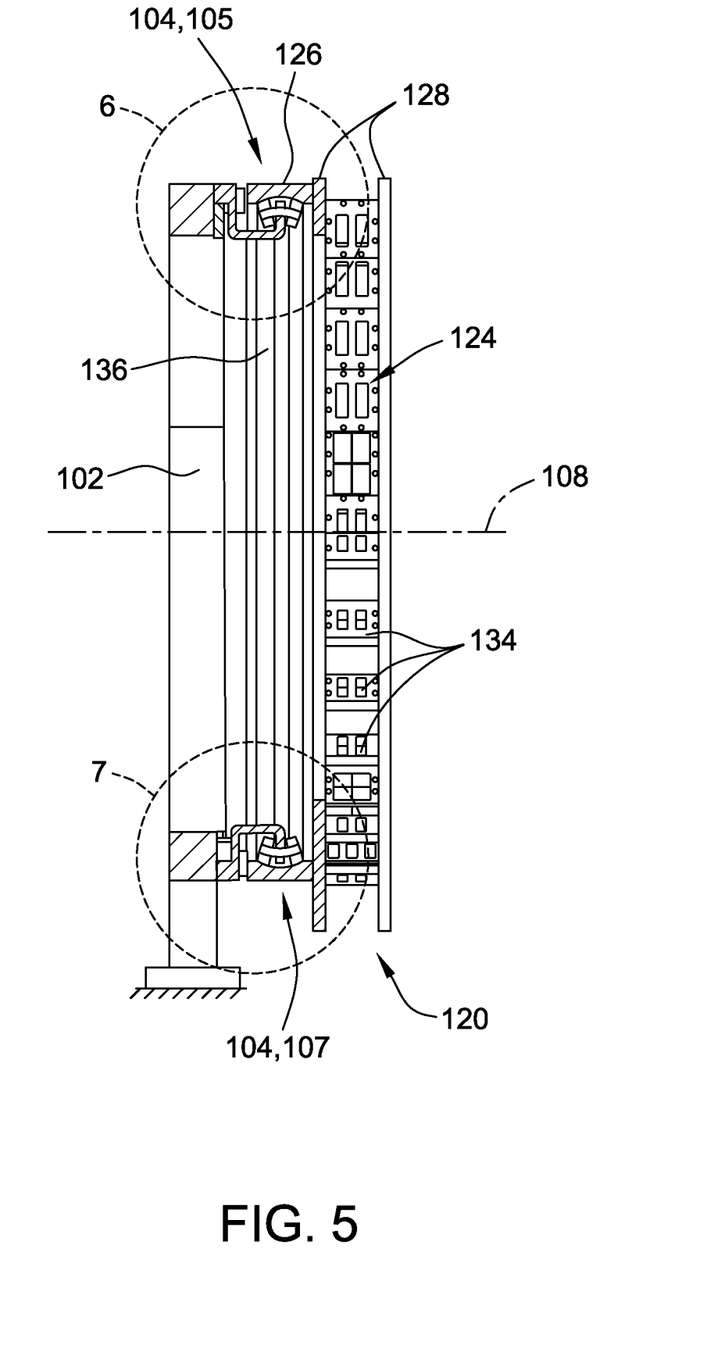
FIG. 5 is a section view of the gantry system of FIGS. 3 and 4 taken along lines 5-5 shown in FIG. 4.

FIG. 3 is a perspective view of an exemplary gantry system 100 suitable for use as gantry system 12 of CT imaging system 10 of FIGS. 1 and 2. FIG. 4 is a rear view of gantry system 100. FIG. 5 is a section view of gantry system 100 taken along lines 5-5 shown in FIG. 4. In the exemplary embodiment, gantry system 100 includes a base 102, a plurality of roller assemblies 104 coupled to base 102, and a gantry assembly 106 rotatably coupled to roller assemblies 104 for rotation about gantry rotational axis 108 relative to base 102. Gantry assembly 106 is rotatably supported by roller assemblies 104, and is configured to rotate about a gantry rotational axis 108 to collect imaging data from an object (not shown in FIG. 3) positioned within a central annular gantry opening 110 defined by gantry assembly 106. Gantry system 100 may also include a drive mechanism (not shown in FIG. 3), such as drive mechanism 30 (FIG. 2), operably coupled to gantry assembly 106 and configured to rotate gantry assembly 106 about gantry rotational axis 108. The drive mechanism may include any suitable equipment for transmitting rotational motion to gantry assembly 106 including, for example and without limitation, gears, drive wheels, drive belts, and combinations thereof. A radial direction 109 is defined at each point on gantry assembly 106 as parallel to a line drawn from gantry rotational axis 108 to that point.

Base 102 provides a fixed support for gantry assembly 106, and includes a perimeter section 116 defining a passage 118 sized to permit the passage of objects, such luggage, therethrough. Base 102 is fixed to a stationary structure, such as the surface or floor 112 of a facility in which gantry system 100 is used (e.g., an airport). An upper portion 101 of base 102 is defined above gantry rotational axis 108, and a lower portion 103 of base 102 is defined below gantry rotational axis 108, where "above" and "below" are defined with respect to a direction of gravitational force. In the exemplary embodiment, base 102 includes two legs 114 each fixed to the stationary structure using suitable fasteners, such as bolts, screws, or pins (not shown). In alternative embodiments, base 102 is fixed to any suitable stationary structure in any suitable fashion that enables gantry system 100 to function as described herein.

Gantry assembly 106 generally includes imaging equipment utilized to capture imaging data of objects positioned within gantry opening 110. In the exemplary embodiment, gantry assembly 106 includes a frame 120, a radiation source 122 coupled to frame 120, a detector array 124 coupled to frame 120, and an annular support rail 126 coupled to frame 120. In alternative embodiments, gantry assembly 106 includes any suitable imaging equipment assembled in any suitable fashion that enables gantry assembly 106 to function as described herein.

In the exemplary embodiment, frame 120 includes two substantially planar plates 128 spaced apart from one another along an axial direction of gantry system 100 (i.e., a direction parallel to gantry rotational axis 108). Each plate defines an annular opening 130 sized to permit the passage of objects, such as luggage, therethrough. Each annular opening 130 at least partially defines gantry opening 110. In the exemplary embodiment, each plate 128 is constructed from steel and is lined with lead. Also in the exemplary embodiment, each plate 128 has substantially the same size and shape, although in other embodiments plates 128 may be sized and shaped differently from one another. In alternative embodiments, frame 120 is constructed from any suitable material and has any suitable arrangement and shaped of components that enables gantry assembly 106 to function as described herein.

Radiation source 122 is configured to emit radiation, such as x-rays, towards detector array 124, which is generally positioned at a diametrically opposite side of frame 120 from radiation source 122. In the exemplary embodiment, radiation source 122 is an x-ray source configured to project a fan beam of x-rays towards detector array 124. In alternative embodiments, radiation source 122 is any suitable source of radiation. In the exemplary embodiment, radiation source 122 is coupled to frame 120 and positioned between plates 128. In alternative embodiments, radiation source 122 is coupled to gantry assembly 106 in any suitable fashion that enables gantry assembly 106 to function as described herein.

Detector array 124 includes a plurality of detector elements 134 (also referred to herein as detectors) arranged in an arcuate pattern generally on a diametrically opposite side of frame 120 from radiation source 122. Each detector element 134 is configured to detect radiation emitted by radiation source 122. In particular, each detector element 134 is configured to produce a signal having a magnitude that represents and is dependent on the intensity of radiation from radiation source 122 incident on detector element 134. In the exemplary embodiment, each detector element 134 is positioned between plates 128 and is coupled to frame 120 using suitable fasteners, such as bolts, screws, pins, and combinations thereof. In alternative embodiments, each detector element 134 is positioned with respect to, and coupled to, gantry assembly 106 in any suitable fashion that enables gantry assembly 106 to function as described herein.

Support rail 126 is coupled to frame 120, and is rotatably coupled to base 102 by roller assemblies 104. Support rail 126 includes an annular, radially inner surface 136 defining a central opening 138 sized to permit the passage of objects, such as luggage, therethrough. Opening 138 at least partially defines gantry opening 110. Support rail 126 is rotatably supported by roller assemblies 104. More specifically, roller assemblies 104 engage radially inner surface 136 of support rail 126. Roller assemblies 104 enable support rail 126 and, more generally, gantry assembly 106 to rotate about gantry rotational axis 108 with respect to base 102 such that gantry system 100 can perform a helical scan on an object that passes through gantry opening 110.

Roller assemblies 104 are disposed substantially within an envelope defined by radially inner and outer surfaces of base 102 with respect to radial direction 109, thus reducing a limitation on a field of view and a tunnel size of CT imaging system 10. For example, a potential location of conveyor belt 16 and a pair of tunnel walls 34 is shown in dashed lines in FIG. 4. Roller assemblies 104 disposed substantially within the envelope defined by base 102 enables a radially outward location of tunnel walls 34 and conveyor belt 16 to be limited only by a size of base 102, thus facilitating an increased field of view and tunnel size of CT imaging system 10 for a given size of base 102.

Plurality of roller assemblies 104 includes at least one upper roller assembly 105 positioned on upper portion 101 of base 102, and at least one lower roller assembly 107 positioned on lower portion 103 of base 102. Because each of the plurality of roller assemblies 104 engages radially inner surface 136, as described above, the at least one upper roller assembly 105 on upper portion 101 substantially supports a weight of gantry assembly 106, while the at least one lower roller assembly 107 on lower portion 103 supports little or none of the weight of gantry assembly 106.

For example, in the exemplary embodiment, plurality of roller assemblies 104 includes three roller assemblies 104. More specifically, the at least one upper roller assembly 105 includes two upper roller assemblies 105 that cooperate to substantially support the weight of gantry assembly 106, and the at least one lower roller assembly 107 includes one lower roller assembly 107. In alternative embodiments, the at least one upper roller assembly 105 and the at least one lower roller assembly 107 each include any suitable number of roller assemblies that enables gantry system 100 to function as described herein.

Figure 6:
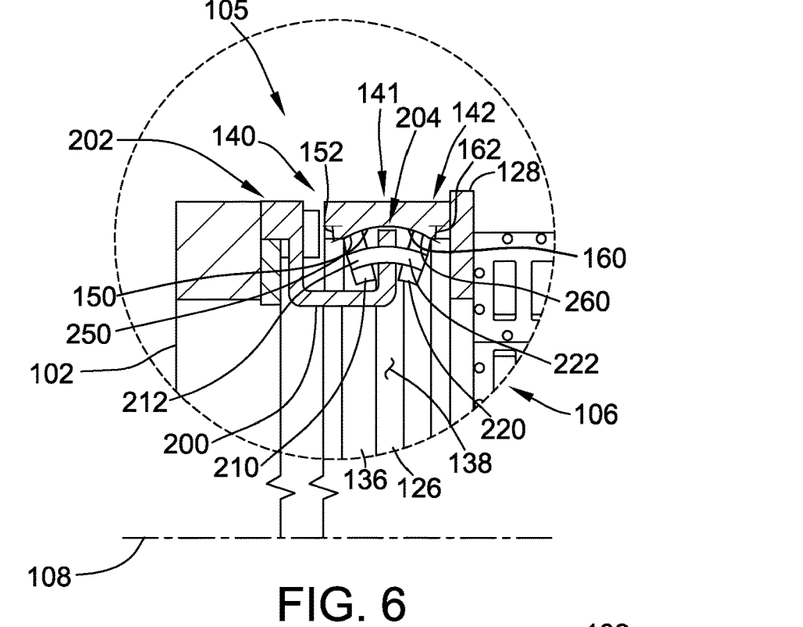
FIG. 6 is a detail view of a first exemplary upper roller assembly shown in FIG. 5.
Figure 7:
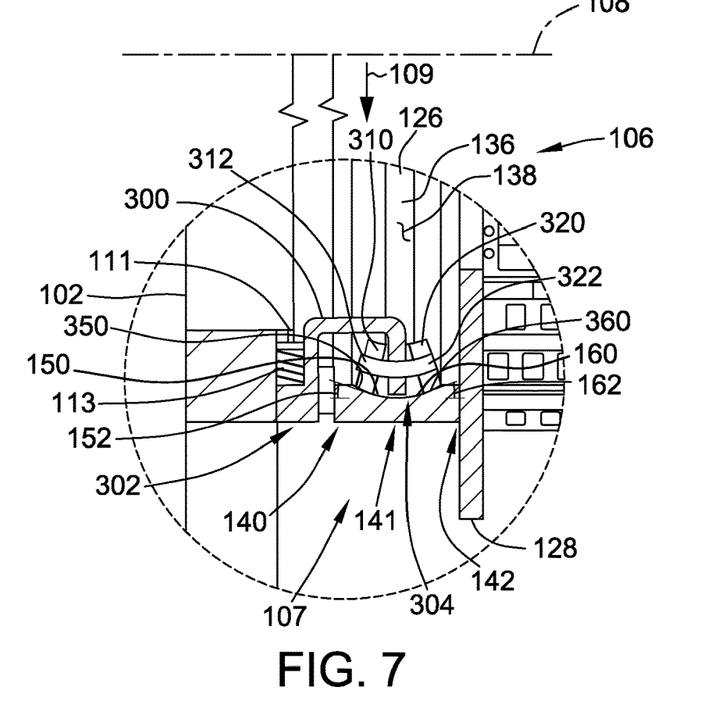
FIG. 7 is a detail view of an exemplary lower roller assembly shown in FIG. 5.
Figure 8:
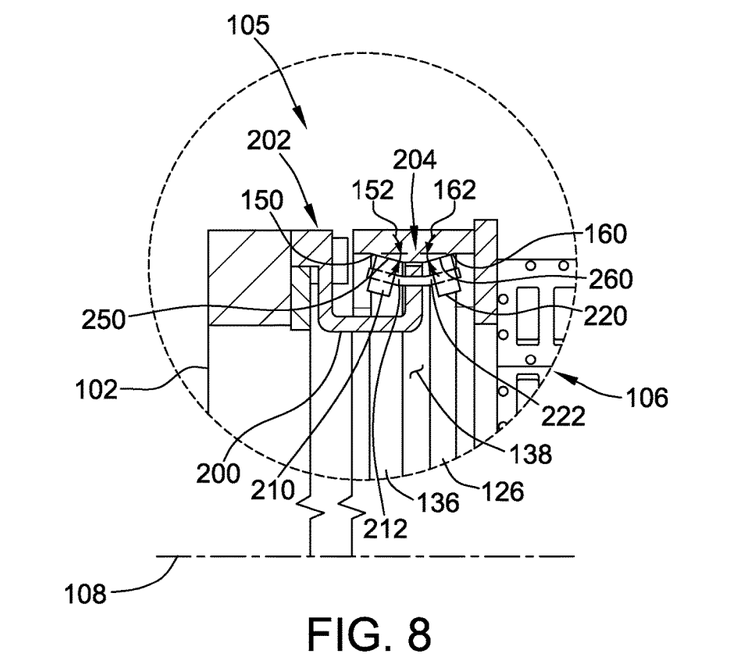
FIG. 8 is a section view of a second exemplary upper roller assembly for use with an alternative exemplary embodiment of a gantry system.
Figure 9:
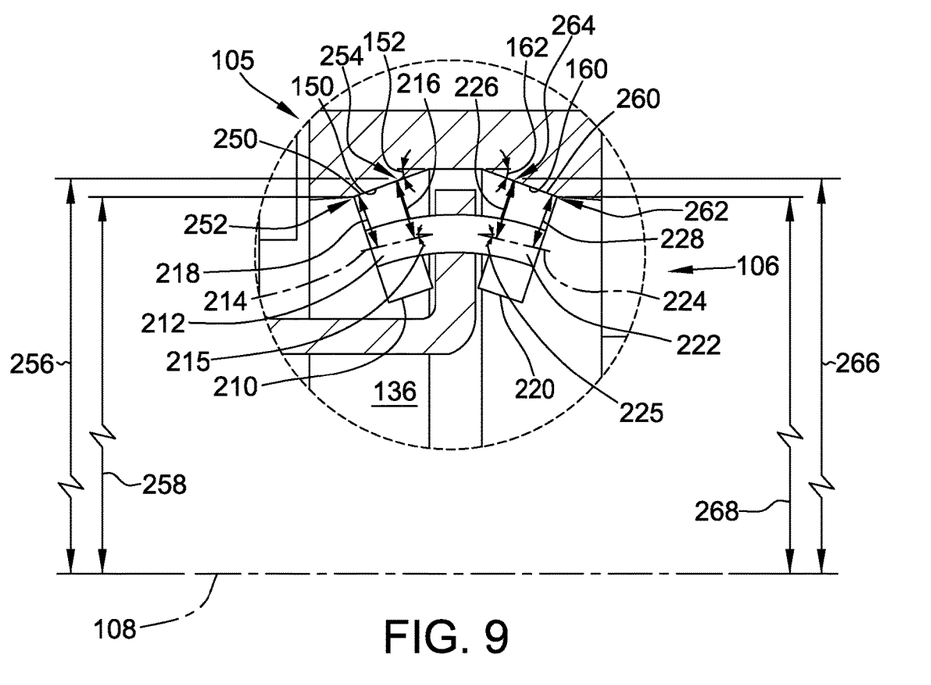
FIG. 9 is an enlarged view of FIG. 6.

FIG. 6 is a detail view of gantry system 100 shown in FIG. 5 and identified therein with the reference numeral 6, and FIG. 7 is a detail view of gantry system 100 shown in FIG. 5 and identified therein with the reference numeral 7. More specifically, FIG. 6 illustrates an exemplary embodiment of upper roller assembly 105 on upper portion 101 of base 102 engaging radially inner surface 136 of support rail 126, and FIG. 7 illustrates an exemplary embodiment of lower roller assembly 107 on lower portion 103 of base 102 engaging radially inner surface 136. FIG. 8 illustrates an alternative embodiment of upper roller assembly 105 engaging radially inner surface 136 of support rail 126 in an alternative embodiment of gantry system 100. FIG. 9 is an enlarged view of a portion of FIG. 6.

Support rail 126 extends in a direction parallel to gantry rotational axis 108 from a first end 140 through an intermediate portion 141 to a second end 142. Radially inner surface 136 includes a first portion 150 that is canted with respect to gantry rotational axis 108, and a second portion 160 that is oppositely canted with respect to gantry rotational axis 108. For example, in the exemplary embodiment shown in FIGS. 6 and 7, first portion 150 is canted radially outward at a first angle 152 between first end 140 and intermediate portion 141, and second portion 160 is oppositely canted radially inward at a second angle 162 between intermediate portion 141 and second end 142. For another example, in the exemplary embodiment shown in FIG. 8, first portion 150 is canted radially inward at first angle 152 between first end 140 and intermediate portion 141, and second portion 160 is oppositely canted radially outward at second angle 162 between intermediate portion 141 and second end 142.

In certain embodiments, second angle 162 is equal and opposite to first angle 152, such that first portion 150 and second portion 160 of radially inner surface 136 are symmetrically disposed about intermediate portion 141. In alternative embodiments, second angle 162 is other than equal and opposite to first angle 152, such that first portion 150 and second portion 160 are other than symmetrically disposed about intermediate portion 141.

With reference to FIGS. 6 and 8, each upper roller assembly 105 includes an arm 200 that extends from a first end 202 to a second end 204. First end 202 is coupled to base 102. In the exemplary embodiment, first end 202 is coupled to base 102 such that first end 202 is substantially fixed relative to base 102. For example, first end 202 is fixedly coupled to base 102 using suitable fasteners, such as bolts, screws, or pins (not shown). In alternative embodiments, first end 202 is coupled to base 102 in such that first end 202 is other than substantially fixed relative to base 102. Arm 200 is configured to support at least a portion of the weight of gantry assembly 106, and to transfer the supported weight through first end 202 to base 102.

Second end 204 of arm 200 extends, in a direction generally parallel to gantry rotational axis 108, into opening 138 defined by support rail 126. A first roller sleeve 210 is rotatably coupled to second end 204 and configured to engage first portion 150, and a second roller sleeve 220 is rotatably coupled to second end 204 and configured to engage second portion 160. For example, in the exemplary embodiment, a first spindle 212 is coupled to arm 200 proximate second end 204, and first roller sleeve 210 is coupled for rotation about first spindle 212. Similarly, a second spindle 222 is coupled to arm 200 proximate second end 204, and second roller sleeve 220 is coupled for rotation about second spindle 222.

An engagement surface 250 of first roller sleeve 210 is defined as the portion of first roller sleeve 210 that is in contact with first portion 150 at any given orientation of first roller sleeve 210 as first roller sleeve 210 rotates, and an engagement surface 260 of second roller sleeve 220 is defined as the portion of second roller sleeve 220 that is in contact with second portion 160 at any given orientation of second roller sleeve 220 as second roller sleeve 220 rotates. Upper roller assembly 105 is configured such that engagement surface 250 of first roller sleeve 210 is substantially parallel to first portion 150 as first roller sleeve 210 rotates, and engagement surface 260 of second roller sleeve 220 is substantially parallel to second portion 160 as second roller sleeve 220 rotates.

With reference to FIG. 9, in certain embodiments, first roller sleeve 210 is configured to rotatably engage first portion 150 of radially inner surface 136 at engagement surface 250 without slipping as gantry assembly 106 rotates about gantry rotational axis 108, and second roller sleeve 220 is configured to rotatably engage second portion 160 of radially inner surface 136 at engagement surface 260 without slipping as gantry assembly 106 rotates about gantry rotational axis 108. More specifically, engagement surface 250 and first portion 150 are in contact between a shared radially innermost point 252 and a shared radially outermost point 254, and engagement surface 260 and second portion 160 are in contact between a shared radially innermost point 262 and a shared radially outermost point 264. As gantry assembly 106 rotates about gantry rotational axis 108 at a selected first angular velocity, radially outermost point 254 of radially inner surface 136 moves with a greater linear velocity than radially innermost point 252, by a ratio equal to a ratio of a distance 258 of radially outermost point 254 from gantry rotational axis 108 to a distance 256 of radially innermost point 252 from gantry rotational axis 108. Similarly, radially outermost point 264 of radially inner surface 136 moves with a greater linear velocity than radially innermost point 262, by a proportion equal to a ratio of a distance 268 of radially outermost point 264 from gantry rotational axis 108 to a distance 266 of radially innermost point 262 from gantry rotational axis 108.

In order for first roller sleeve 210 to engage first portion 150 without slipping, first roller sleeve 210 rotates at a selected second angular velocity that is complementary to the selected first angular velocity of gantry assembly 106, such that linear velocities of radially innermost point 252 and radially outermost point 254 of engagement surface 250 match the linear velocities of radially innermost point 252 and radially outermost point 254 of radially inner surface 136. More specifically, first roller sleeve 210 has a frusto-conical shape symmetric about an axis 214 of first spindle 212, such that a ratio of a distance 216, defined between radially outermost point 254 of engagement surface 250 and first spindle axis 214, and a distance 218, defined between radially innermost point 252 of engagement surface 250 and first spindle axis 214, matches the ratio of distance 258 to distance 256. First spindle axis 214 is disposed at an angle 215 with respect to gantry rotational axis 108 such that engagement surface 250 of first roller sleeve 210 is substantially parallel to first portion 150.

Similarly, in order for second roller sleeve 220 to engage second portion 160 without slipping, second roller sleeve 220 rotates at a selected third angular velocity that is complementary to the selected first angular velocity of gantry assembly 106, such that linear velocities of radially innermost point 262 and radially outermost point 264 of engagement surface 260 match the linear velocities of radially innermost point 262 and radially outermost point 264 of radially inner surface 136. More specifically, second roller sleeve 220 has a frusto-conical shape symmetric about an axis 224 of second spindle 222, such that a ratio of a distance 226, defined between radially outermost point 264 of engagement surface 260 and second spindle axis 224, and a distance 228, defined between radially innermost point 262 of engagement surface 260 and second spindle axis 224, matches the ratio of distance 268 to distance 266. Second spindle axis 224 is disposed at an angle 225 with respect to gantry rotational axis 108 such that engagement surface 260 of second roller sleeve 220 is substantially parallel to second portion 160.

In certain embodiments in which second angle 162 is equal and opposite to first angle 152, the third angular velocity is equal to the second angular velocity, the frusto-conical shapes of roller sleeves 210 and 220 are substantially identical, and angle 215 of first spindle 212 is substantially equal to angle 225 of second spindle 222.

In embodiments such as that illustrated in FIG. 8, in which first portion 150 is canted radially inward at first angle 152 between first end 140 and intermediate portion 141, and second portion 160 is oppositely canted radially outward at second angle 162 between intermediate portion 141 and second end 142, radially innermost points 252 and 262 are located proximate to intermediate portion 141, and radially outermost points 254 and 264 are located proximate to first end 140 and second end 142, respectively. It should be understood that proportional relationships similar to those described with reference to FIG. 9 are applicable to achieve non-slip rotational engagement in embodiments such as that illustrated in FIG. 8.

In alternative embodiments, upper roller assembly 105 is configured in any other suitable fashion such that first roller sleeve 210 rotatably engages first portion 150 without slipping, and second roller sleeve 220 rotatably engages second portion 160 of radially inner surface 136 without slipping, as gantry assembly 106 rotates about gantry rotational axis 108.

With reference to FIG. 7, lower roller assembly 107 includes an arm 300 that extends from a first end 302 to a second end 304. First end 302 is coupled to base 102 such that lower roller assembly 107 is movable relative to base 102 in a direction parallel to radial direction 109. For example, in the exemplary embodiment, first end 302 is coupled for sliding movement along a pin 111 fixed to base 102 and disposed parallel to radial direction 109. In addition, first end 302 is coupled to base 102 such that lower roller assembly 107 is biased radially outward relative to base 102 in a direction parallel to radial direction 109. For example, in the exemplary embodiment, a spring 113 is coupled between base 102 and first end 302 and maintained in a compressed state, such that spring 113 biases lower roller assembly 107 radially outward relative to base 102. In alternative embodiments, lower roller assembly 107 is coupled to base 102 in any other suitable fashion such that lower roller assembly 107 is movable, and biased radially outward, relative to base 102 in a direction parallel to radial direction 109.

Second end 304 of arm 300 extends, in a direction generally parallel to gantry rotational axis 108, into opening 138 defined by support rail 126. A first roller sleeve 310 is rotatably coupled to second end 304 and configured to engage first portion 150, and a second roller sleeve 320 is rotatably coupled to second end 304 and configured to engage second portion 160. For example, in the exemplary embodiment, a first spindle 312 is coupled to arm 300 proximate second end 304, and first roller sleeve 310 is coupled for rotation about first spindle 312. Similarly, a second spindle 322 is coupled to arm 300 proximate second end 304, and second roller sleeve 320 is coupled for rotation about second spindle 322.

As with roller sleeves 210 and 220 described above, an engagement surface 350 of first roller sleeve 310 is defined as the portion of first roller sleeve 310 that is in contact with first portion 150 at any given orientation of first roller sleeve 310 as first roller sleeve 310 rotates, and an engagement surface 360 of second roller sleeve 320 is defined as the portion of second roller sleeve 320 that is in contact with second portion 160 at any given orientation of second roller sleeve 320 as second roller sleeve 320 rotates. Lower roller assembly 107 is configured such that engagement surface 350 of first roller sleeve 310 is substantially parallel to first portion 150 as first roller sleeve 310 rotates, and engagement surface 360 of second roller sleeve 320 is substantially parallel to second portion 160 as second roller sleeve 320 rotates.

Also as with roller sleeves 210 and 220 described above, in certain embodiments, first roller sleeve 310 is configured to rotatably engage first portion 150 of radially inner surface 136 at engagement surface 350 without slipping as gantry assembly 106 rotates about gantry rotational axis 108, and second roller sleeve 320 is configured to rotatably engage second portion 160 of radially inner surface 136 at engagement surface 360 without slipping as gantry assembly 106 rotates about gantry rotational axis 108. More specifically, each of roller sleeves 310 and 320 has a frusto-conical shape symmetric about axes (not numbered) of respective spindles 312 and 322, and proportional relationships similar to those described with reference to roller sleeves 210 and 220 are applicable to achieve non-slip rotational engagement for roller sleeves 310 and 320. In addition, although an embodiment of lower roller assembly 107 is not illustrated for embodiments such as that illustrated in FIG. 8, in which first portion 150 is canted radially inward at first angle 152 between first end 140 and intermediate portion 141, and second portion 160 is oppositely canted radially outward at second angle 162 between intermediate portion 141 and second end 142, it should be understood that a suitable lower roller assembly 107, complementary to the embodiment of upper roller assembly 105 shown in FIG. 8, can similarly be provided for such embodiments.

Figure 10:
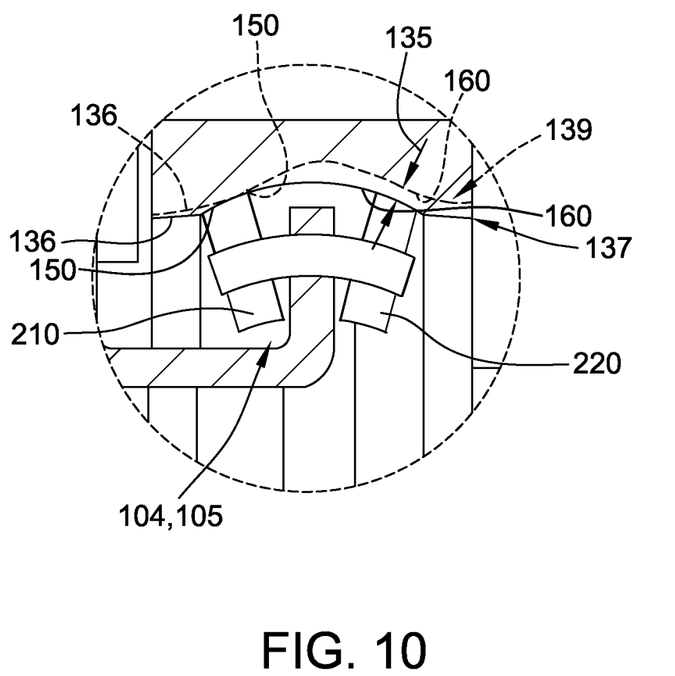
FIG. 10 is a schematic illustration of an exemplary design operating alignment and a perturbed alignment of the upper roller assembly of FIG. 6.

In certain embodiments, oppositely canted first and second portions 150 and 160 facilitate maintaining an alignment of gantry assembly 106 as it rotates about gantry rotational axis 108. More specifically, FIG. 10 is a schematic illustration of a design operating alignment 137 of one of upper roller assemblies 105 relative to surface 136, illustrated in solid lines, and of a perturbed alignment 139 of the one of upper roller assemblies 105 relative to surface 136, illustrated schematically in dashed lines and resulting from a perturbation of gantry assembly 106 relative to base 102. In design operating alignment 137, first roller sleeve 210 is in contact with first portion 150 and second roller sleeve 220 is in contact with second portion 160. Perturbed alignment 139 causes second portion 160 to lose contact with second roller sleeve 220, as illustrated by gap 135. Alternatively, perturbed alignment 139 causes first portion 150 to lose contact (not shown) with first roller sleeve 210. At least one of a weight of gantry assembly 106 and a radially outward bias applied by lower roller assembly 107 tends to cause gantry assembly 106 to shift back from perturbed alignment 139 to design operating alignment 137. Thus, oppositely disposed first angle 152 and second angle 162 of first portion 150 and second portion 160, respectively, facilitate self-alignment of gantry assembly 106 with respect to base 102 during operation of gantry system 100.

In certain embodiments, each of first angle 152 and second angle 162 is in a range of between about 5° and about 60°. In some such embodiments, each of first angle 152 and second angle 162 is in a range of between about 10° and about 45°. Moreover, in some such embodiments, each of first angle 152 and second angle 162 is in a range of between about 10° and about 30°. In the exemplary embodiment, each of first angle 152 and second angle 162 is about 20°.

Moreover, in certain embodiments, lower roller assembly 107 being movable, and biased radially outward, relative to base 102 in a direction parallel to radial direction 109 further facilitates stable rotation of gantry assembly 106 about gantry rotational axis 108. More specifically, the radially outward bias compensates for local or global changes in a diameter of radially inner surface 136 relative to a position of roller assemblies 104 during operation of gantry system 100. Such changes in diameter may arise due to at least one of wear on roller assemblies 104, wear on radially inner surface 136, thermal expansion/contraction of surface 136 in changing ambient operational conditions, and perturbations due to any other cause. Lower roller assembly 107 being movable, and biased radially outward, relative to base 102 facilitates maintaining stable contact between radially inner surface 136 and each of roller assemblies 104 throughout such changes in diameter of radially inner surface 136 relative to roller assemblies 104 during operation of gantry system 100, further facilitating the self-alignment of gantry assembly 106 described above.

In addition, in some embodiments, the stability and self-aligning characteristics of gantry system 100 described above are achieved using commercial, off the shelf components for each of roller assemblies 104. Furthermore, in some embodiments, the stability and self-aligning characteristics of gantry system 100 described above are achieved using only two upper roller assemblies 105 and one lower roller assembly 107. Thus, both an initial cost and a lifetime maintenance cost of gantry system 100 are greatly reduced. In alternative embodiments, at least one of roller assemblies 104 does not use commercial, off the shelf components, and/or gantry system 100 uses more than two upper roller assemblies 105 and/or more than one lower roller assembly 107. Also, in certain embodiments, roller assemblies 104 are disposed substantially within a spatial envelope defined by gantry assembly 106 and base 102, which facilitates reducing a footprint of gantry system 100.

Figure 11:
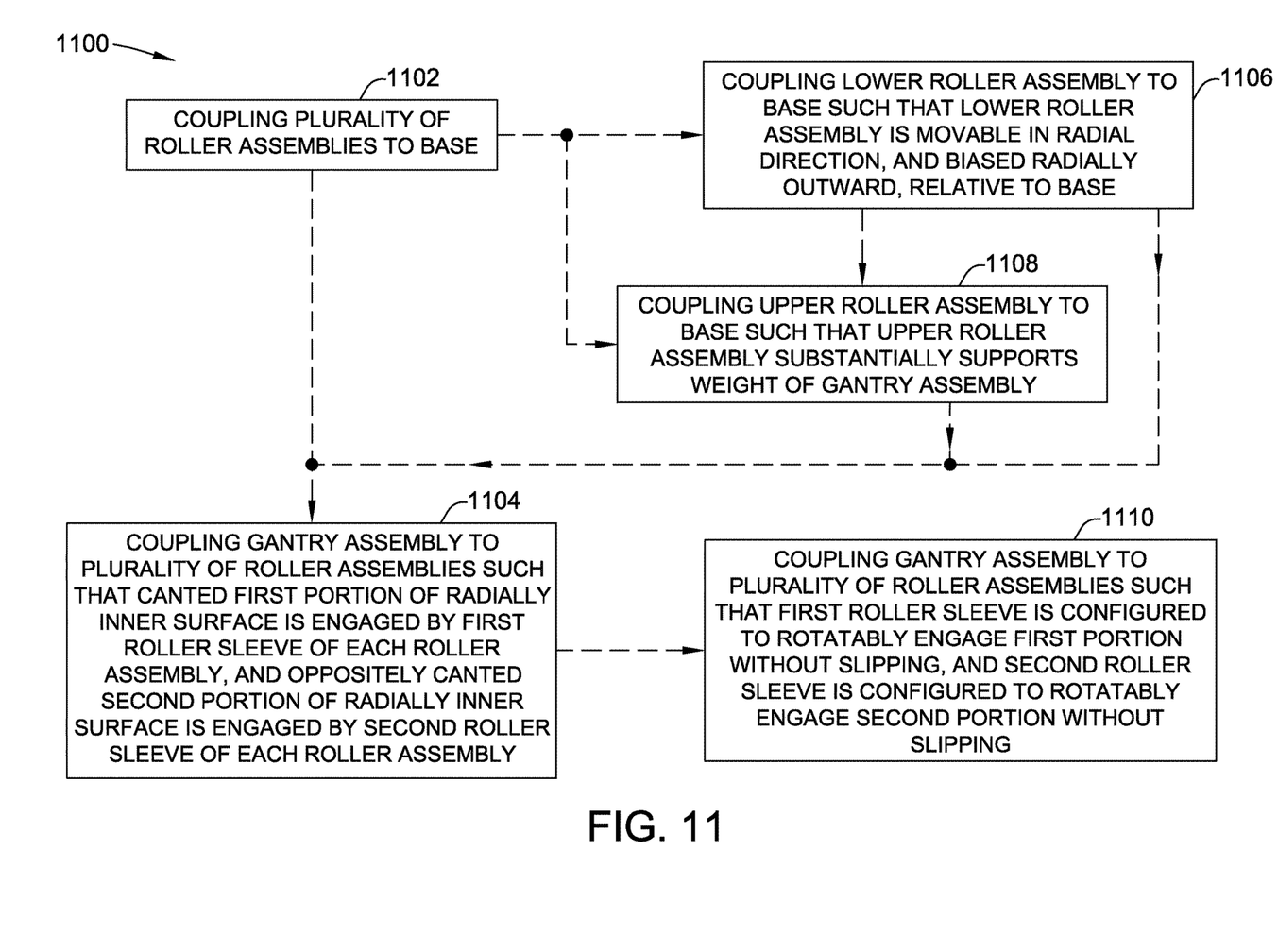
FIG. 11 is a flow chart of an exemplary method of assembling a CT imaging system.

FIG. 11 is a flow chart of an exemplary method 1100 of assembling a CT imaging system, such as CT imaging system 10. With reference also to FIGS. 1-9, the CT imaging system includes a base, such as base 102. Method 1100 includes coupling 1102 a plurality of roller assemblies, such as roller assemblies 104, to the base. Each of the plurality of roller assemblies comprises a first roller sleeve and a second roller sleeve, such as first roller sleeve 210 or 310 and second roller sleeve 220 or 320. Method 1100 also includes coupling 1104 a gantry assembly, such as gantry assembly 106, to the plurality of roller assemblies such that a canted first portion of a radially inner surface of a support rail of the gantry assembly, such as first portion 150 of radially inner surface 136 of support rail 126, is engaged by the first roller sleeve of each roller assembly, and an oppositely canted second portion of the radially inner surface, such as second portion 160, is engaged by the second roller sleeve of each roller assembly.

In some embodiments, the plurality of roller assemblies includes at least one lower roller assembly, such as lower roller assembly 107, and the step of coupling 1102 the plurality of roller assemblies to the base further includes coupling 1106 the at least one lower roller assembly to the base such that the at least one lower roller assembly is movable in a radial direction, such as radial direction 109, and biased radially outward, relative to the base. Additionally or alternatively, the plurality of roller assemblies includes at least one upper roller assembly, such as upper roller assembly 105, and the step of coupling 1102 the plurality of roller assemblies to the base further includes coupling 1108 the at least one upper roller assembly to the base such that the at least one upper roller assembly substantially supports a weight of the gantry assembly.

In certain embodiments, the step of coupling 1104 the gantry assembly to the plurality of roller assemblies further includes coupling 1110 the gantry assembly to the plurality of roller assemblies such that the first roller sleeve is configured to rotatably engage the first portion without slipping as the gantry assembly rotates about the rotational axis, and the second roller sleeve is configured to rotatably engage the second portion without slipping as the gantry assembly rotates about the rotational axis.

Embodiments of the systems and methods described herein facilitate assembling and maintaining gantry systems used in CT imaging systems, and further facilitate reducing the part count and overall cost of gantry systems used in CT imaging systems. For example, the embodiments described herein include a gantry assembly rotatably supported by a plurality of roller assemblies. The gantry assembly includes a support rail inner surface that has oppositely canted first and second portions, and each roller assembly includes a first roller sleeve that engages the first portion and a second roller sleeve that engages the second portion. The embodiments described herein thereby facilitate self-alignment of the gantry system with respect to a base of CT imaging systems. In addition, the embodiments include at least one upper roller assembly that substantially supports a weight of gantry assembly, and at least one lower roller assembly that is movable in a radial direction, and biased radially outward, relative to a base of the CT imaging system, further facilitating self-alignment of the gantry system. Moreover, the rollers of the gantry systems described herein are not enclosed within a bearing enclosure (e.g., between two bearing rings), and are thus readily accessible for inspection, repairs, and replacement. Further, the described herein may include commercial, off-the-shelf roller components that are not custom designed for a particular CT imaging system. The gantry systems described herein thereby facilitate reducing the time and cost associated with maintaining gantry systems of CT imaging systems.

Exemplary technical effects of the systems and methods described herein include at least one of: (a) improving an alignment accuracy of rotatable gantry systems used in CT imaging systems; (b) reducing the overall part count and cost of rotatable gantry systems used in CT imaging systems; and (c) reducing the cost and time associated with repairing, replacing, and maintaining gantry systems used in CT imaging systems.

Exemplary embodiments of gantry systems for CT imaging systems and methods of assembling gantry systems are described above in detail. The methods and systems are not limited to the specific embodiments described herein, but rather, components of systems and/or steps of the methods may be utilized independently and separately from other components and/or steps described herein. Accordingly, the exemplary embodiment can be implemented and utilized in connection with many other applications not specifically described herein.

A computer, such as those described herein, includes at least one processor or processing unit and a system memory. The computer typically has at least some form of computer readable media. By way of example and not limitation, computer readable media include computer storage media and communication media. Computer storage media include volatile and nonvolatile, removable and nonremovable media implemented in any method or technology for storage of information such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Combinations of any of the above are also included within the scope of computer readable media.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A gantry system for use with a computed tomography (CT) imaging system, said gantry system comprising:
   a gantry assembly configured to rotate about a rotational axis to collect imaging data from an object, said gantry assembly comprises a support rail including a radially inner surface including a canted first portion and an oppositely canted second portion; and
   a plurality of roller assemblies rotatably supporting said gantry assembly, each of said plurality of roller assemblies comprises a first roller sleeve configured to engage said first portion and a second roller sleeve configured to engage said second portion.

2. The gantry system of claim 1, wherein said plurality of roller assemblies comprises at least one lower roller assembly that is movable in a radial direction, and biased radially outward, relative to a base of the CT imaging system.

3. The gantry system of claim 1, wherein said plurality of roller assemblies comprises at least one upper roller assembly that substantially supports a weight of said gantry assembly.

4. The gantry system of claim 1, wherein said first portion and said second portion are symmetrically disposed about an intermediate portion of said support rail.

5. The gantry system of claim 1, wherein each said roller assembly further comprises an arm that is substantially within an envelope defined by a base of said gantry system, said arm extends from a first end to a second end, said first end is coupled to a base of the CT imaging system, and said first and second roller sleeves are rotatably coupled to said second end.

6. The gantry system of claim 1, wherein said first roller sleeve is configured to rotatably engage said first portion without slipping as said gantry assembly rotates about the rotational axis, and said second roller sleeve is configured to rotatably engage said second portion without slipping as said gantry assembly rotates about the rotational axis.

7. The gantry system of claim 5, wherein each said roller assembly further comprises:
   a first spindle coupled to said arm proximate said second end, wherein said first roller sleeve is coupled for rotation about said first spindle and has a first frusto-conical shape symmetric about said first spindle; and
   a second spindle coupled to said arm proximate said second end, wherein said second roller sleeve is coupled for rotation about said second spindle and has a second frusto-conical shape symmetric about said second spindle.

8. The gantry system of claim 7, wherein said first spindle is disposed at a first angle with respect to the rotational axis such that an engagement surface of said first roller sleeve is substantially parallel to said first portion, and said second spindle is disposed at a second angle with respect to the rotational axis such that an engagement surface of said second roller sleeve is substantially parallel to said second portion.

9. A computed tomography (CT) imaging system comprising:
   a base;
   a plurality of roller assemblies coupled to said base, each of said plurality of roller assemblies comprises a first roller sleeve and a second roller sleeve; and
   a gantry assembly rotatably coupled to said plurality of roller assemblies for rotation about a rotational axis, said gantry assembly comprising:
   a radiation source;
   at least one detector configured to detect radiation emitted by said radiation source; and
   a support rail comprising a radially inner surface including a canted first portion engaged by said first roller sleeve of each said roller assembly and an oppositely canted second portion engaged by said second roller sleeve of each said roller assembly.

10. The CT imaging system of claim 9, wherein said plurality of roller assemblies comprises at least one lower roller assembly that is movable in a radial direction, and biased radially outward, relative to said base.

11. The CT imaging system of claim 9, wherein said plurality of roller assemblies comprises at least one upper roller assembly that substantially supports a weight of said gantry assembly.

12. The CT imaging system of claim 9, wherein said first portion and said second portion are symmetrically disposed about an intermediate portion of said support rail.

13. The CT imaging system of claim 9, wherein each said roller assembly further comprises an arm that is substantially within an envelope defined by said base, said arm extends from a first end to a second end, said first end is coupled to said base, and said first and second roller sleeves are rotatably coupled to said second end.

14. The CT imaging system of claim 9, wherein said first roller sleeve is configured to rotatably engage said first portion without slipping as said gantry assembly rotates about the rotational axis, and said second roller sleeve is configured to rotatably engage said second portion without slipping as said gantry assembly rotates about the rotational axis.

15. The CT imaging system of claim 13, wherein each said roller assembly further comprises:
   a first spindle coupled to said arm proximate said second end, wherein said first roller sleeve is coupled for rotation about said first spindle and has a first frusto-conical shape symmetric about said first spindle; and
   a second spindle coupled to said arm proximate said second end, wherein said second roller sleeve is coupled for rotation about said second spindle and has a second frusto-conical shape symmetric about said second spindle.

16. The CT imaging system of claim 15, wherein said first spindle is disposed at a first angle with respect to the rotational axis such that an engagement surface of said first roller sleeve is substantially parallel to said first portion, and said second spindle is disposed at a second angle with respect to the rotational axis such that an engagement surface of said second roller sleeve is substantially parallel to said second portion.

17. A method of assembling a CT imaging system including a base, said method comprising:
   coupling a plurality of roller assemblies to the base, each of the plurality of roller assemblies comprises a first roller sleeve and a second roller sleeve; and
   coupling a gantry assembly to the plurality of roller assemblies such that a canted first portion of a radially inner surface of a support rail of the gantry assembly is engaged by the first roller sleeve of each roller assembly, and an oppositely canted second portion of the radially inner surface is engaged by the second roller sleeve of each roller assembly.

18. The method of claim 17, wherein the plurality of roller assemblies comprises at least one lower roller assembly, said coupling the plurality of roller assemblies to the base further comprises coupling the at least one lower roller assembly to the base such that the at least one lower roller assembly is movable in a radial direction, and biased radially outward, relative to the base.

19. The method of claim 17, wherein the plurality of roller assemblies comprises at least one upper roller assembly, said coupling the plurality of roller assemblies to the base further comprises coupling the at least one upper roller assembly to the base such that the at least one upper roller assembly substantially supports a weight of the gantry assembly.

20. The method of claim 17, wherein said coupling the gantry assembly to the plurality of roller assemblies further comprises coupling the gantry assembly to the plurality of roller assemblies such that said first roller sleeve is configured to rotatably engage said first portion without slipping as said gantry assembly rotates about a rotational axis, and said second roller sleeve is configured to rotatably engage said second portion without slipping as said gantry assembly rotates about the rotational axis.

* * * * *